US009198865B2

(12) United States Patent
Hall et al.

(10) Patent No.: US 9,198,865 B2
(45) Date of Patent: Dec. 1, 2015

(54) BIOLOGICALLY ACTIVE COMPOSITION COMPRISING ETHYLCELLULOSE

(75) Inventors: Mark J. Hall, Midland, MI (US); Karen A. Coppens, Midland, MI (US); Pamela S. Larsen, North Brunswick, NJ (US); Shawn A. Mitchell, Midland, MI (US); Michael D. Read, Midland, MI (US); Uma Shrestha, Bay City, MI (US)

(73) Assignee: Dow Global Technologies LLC

( * ) Notice: Subject to any disclaimer, the term of this patent is extended or adjusted under 35 U.S.C. 154(b) by 1028 days.

(21) Appl. No.: 12/161,255

(22) PCT Filed: Nov. 17, 2006

(86) PCT No.: PCT/US2006/044557
§ 371 (c)(1),
(2), (4) Date: Dec. 31, 2008

(87) PCT Pub. No.: WO2007/084212
PCT Pub. Date: Jul. 26, 2007

(65) Prior Publication Data
US 2009/0130058 A1    May 21, 2009

Related U.S. Application Data

(60) Provisional application No. 60/760,253, filed on Jan. 19, 2006, provisional application No. 60/788,938, filed on Apr. 4, 2006.

(51) Int. Cl.
*A61K 38/21* (2006.01)
*A61P 31/12* (2006.01)
*A61K 9/20* (2006.01)
*A61K 9/70* (2006.01)

(52) U.S. Cl.
CPC ............ *A61K 9/2095* (2013.01); *A61K 9/2031* (2013.01); *A61K 9/2054* (2013.01); *A61K 9/7007* (2013.01)

(58) Field of Classification Search
None
See application file for complete search history.

(56) References Cited

U.S. PATENT DOCUMENTS

| 2,257,104 | A |  | 9/1941 | Burrows et al. |  |
| 3,941,865 | A |  | 3/1976 | Miller et al. |  |
| 4,645,812 | A |  | 2/1987 | Maier |  |
| 4,678,516 | A |  | 7/1987 | Alderman et al. |  |
| RE33,093 | E | * | 10/1989 | Schiraldi et al. | 424/676 |
| 5,432,215 | A |  | 7/1995 | Grig et al. |  |
| 5,966,582 | A |  | 10/1999 | Chalasani et al. |  |
| 6,375,963 | B1 | * | 4/2002 | Repka | A61K 9/006 424/402 |
| 6,488,963 | B1 |  | 12/2002 | McGinty et al. |  |
| 8,298,581 | B2 | * | 10/2012 | Fischer et al. | 424/480 |
| 2003/0044446 | A1 | * | 3/2003 | Moro et al. | 424/426 |
| 2005/0037055 | A1 |  | 2/2005 | Yang et al. |  |

FOREIGN PATENT DOCUMENTS

| EP | 0 504 870 | 9/1996 |
| WO | WO 97/49384 | 12/1997 |
| WO | WO 00/15261 | 3/2000 |
| WO | WO 01/62229 | 8/2001 |
| WO | WO 02/35991 | 5/2002 |

OTHER PUBLICATIONS

Coppens et al., "The Effect of Polymeric Excipient Selection and Process Variables on Hot Melt Extrusion for Solid Dosage Forms".
Coppens et al.., "Hot Melt Extrusion: Effect of Polymer Selection and Processing on Drug Dissolution", $32^{nd}$ Annual Meeting of the Controlled Release Society, Jun. 18-22, 2005.
Coppens et al.., "Hot Melt Extrusion of Ketoprofen: Effect of Polymeric Exipient Selection", Annual Meeting and Exposition of the American Association of Pharmaceutical Scientists, Nov. 6-10, 2005.
Coppens et al.., "Thermal and Rheological Evaluation of Pharmaceutical Excipients for Hot Melt Extrusion", Annual Meeting and Exposition of the American Association of Pharmaceutical Scientists, Nov. 7-9, 2004.
Coppens et al., "Hypromellose, Ethylcellulose, and Polyethylene Oxide Use in Hot Melt Extrusion", Pharmaceutical Technology, Jan. 1, 2006.
Mehuys et al., "In Vitro and In Vivo Evaluation of a Matrix-In-Cylinder System for Sustained Drug Delivery", Journal of Controlled Release, 2004, 261-271, 96.
Mehuys et al., "Hot-Melt Extruded Ethylcellulose Cylinders Containing a HPMC-GELUCIRE® Core for Sustained Drug Delivery", Journal of Controlled Release, 2004, 273-280, 94.
Six et al. "Characterization of Solid Dispersions of Itraconazole and Hydroxypropylmethylcellulose Prepared by Melt Extrusion, Part II," Pharmaceutical Research, 2003,1047-1054, 20 (7).
Verreck et al., "Characterization of Solid Dispersions of Itraconazole and Hydroxypropylmethylcellulose Prepared by Melt Extrusion—Part I," International Journal of Pharmaceutics, 2003, 165-174, 251.
Crowley et al., "Physicochemical Properties and Mechanism of Drug Release from Ethyl Cellulose Matrix Tablets Prepared by Direct Compression and Hot-Melt Extrusion," International Journal of Pharmaceutics, 2004, 509-522, 269.
De Brabander et al., "Bioavailability of Ibuprofen From Hot-Melt Extruded Mini-Matrices," International Journal of Pharmaceutics, 2004, 77-84, 271.
De Brabander et al., "Development and Evaluation of Sustained Release Mini-Matrices Prepared via Hot Melt Extrusion," Journal of Controlled Release, 2003, 235-247, 89.
Schachter et al., "Solid-State Nuclear Magnetic Resonance Characterization of Melt-Prepared Dispersions Based on POLYOX™ WSR", $30^{th}$ Annual Meeting of the Controlled Release Society, Jul. 19-23, 2003.

(Continued)

Primary Examiner — Robert A Wax
Assistant Examiner — Danah Al-Awadi

(57) ABSTRACT

A biologically active composition comprising an ethylcellulose, a polyethylene oxide and a biologically active ingredient, wherein the amount of ethylcellulose is at least about (15) percent, based on the total weight of the composition, can be used in melt-extrusion processes to produce pharmaceutical dosage forms.

7 Claims, 4 Drawing Sheets

(56) References Cited

OTHER PUBLICATIONS

Schachter et al., "Solid Solution of a Poorly Soluble Model Drug in a Phase-Separated Polymer Matrix: Melt-Prepared Dispersions based on POLYOX™ WSR," 30th Annual Meeting of the Controlled Release Society, Jul. 19-23, 2003.
Repka et al., "Production and Characterization of Hot Melt Extruded Films Containing Clotrimazole," Drug Development and Industrial Pharmacy, 2003, 757-765, 29.
Zhang et al., "Properties of Sustained-Release Tablets Prepared by Hot-Melt Extrusion," Pharmaceutical Development and Technology, 1999, 241-250, 42.
Crowley et al., "Stability of Polyethylene Oxide in Matrix Tablets Prepared by Hot-Melt Extrusion," Biomaterials, 2002, 4241-4248, 21.
Repka et al., "Influence of Vitamin E TPGS on the Properties of Hydrophilic Films Produced by Hot-Melt Extrusion", International Journal of Pharmaceutics, 2000, 63-70, 202.
Sadeghi et al., "Influence of Polymer Viscosity and Plasticizer Addition on Ethylcellulose Matrix Characteristics Prepared from Solid Dispersion System", S.I.P Pharma Sciences, 2003, 105-110, 13.
Rambali et al., "Itraconazole Formulation Studies of the Melt-Extrusion Process with Mixture Design", Drug Development and Industrial Pharmacy, 2003, 641-652, 29, 6.
De Brabander et al., "Characterization of Ibuprofen as a Nontraditional Plasticizer of Ethyl Cellulose", Journal of Pharmaceutical Sciences, Jul. 2002, 1678-1685, 91, 7.
McGinity et al., "Hot-Melt Extrusion as a Pharmaceutical Process", American Pharmaceutical Review, 1-8.
McGinity et al., "Hot-Melt Extrusion as a Pharmaceutical Process", AAPS Newsmagazine, Mar. 2004, 21-25.
Sethia et al., "Solid Dispersions: Revival with Greater Possibilities and Applications in Oral Drug Delivery", Critical Review™ In Therapeutic Drug Carrier Systems, 2003, 215-247, 20.
Breitenbach et al., "Melt Extrusion: from Process to Drug Delivery Technology," European Journal of Pharmaceutics and Biopharmaceutics, 2002, 107-117, 54.
Hall et al., "Hot Melt Extrusion (HME)", Nov. 4, 2004.

\* cited by examiner

BIOLOGICALLY ACTIVE COMPOSITION COMPRISING ETHYLCELLULOSE

CROSS REFERENCE STATEMENT

This application claims the benefit of U.S. Provisional Application Nos. 60/760,253, filed Jan. 19, 2006 and U.S. Provisional Application No. 60/788,938, filed Apr. 4, 2006.

FIELD OF THE INVENTION

The present invention relates to the field of melt extrudable biologically active compositions comprising ethylcellulose. The compositions are useful for providing controlled delivery of biologically active ingredients.

BACKGROUND OF THE INVENTION

Hot-melt extrusion as a method for producing sustained-release pharmaceutical formulations that are based on water-soluble polymers, such as polyethylene oxides, poly(meth-acrylate) derivatives, poly(ethylene-co-vinyl acetates), poly (vinyl acetate-co-methacrylic acids), epoxy resins and caprolactones is known. The International Patent Publication WO 97/49384 discloses pharmaceutical formulations comprising a hot-melt extrudable mixture of a therapeutic compound and a high molecular weight poly(ethylene oxide). International Patent Publication WO 02/35991 discloses active agent-containing spherical particles produced by a hot-melt extrusion/spheronization process. A large variety of thermoformable polymeric materials is listed for the production of the particles, such as wax, proteins, cellulosic polymers, polyols, acrylic polymers, fats, glycerin, lipids, fatty acids, fatty alcohols, carbomers, polyvinyl polymers and combinations thereof. U.S. Pat. No. RE 33,093 discloses a bioadhesive extruded single or multi-layered thin film comprising 20 to 92 percent by weight of a hydroxypropyl cellulose, 5 to 60 percent by weight of a homopolymer of ethylene oxide, 0-10 percent by weight of a water-insoluble polymer such as ethylcellulose, propyl cellulose, polyethylene, and polypropylene, and 2-10 percent of a plasticizer.

It would be desirable to provide new sustained-release compositions of which the release rate of the biologically active ingredient can be varied and/or controlled, particularly that the release rate of the biologically active ingredient can be adjusted to the specific need of administering the biologically active ingredient or to the specific biologically active ingredient.

SUMMARY OF THE INVENTION

One aspect of the present invention is a biologically active composition comprising an ethylcellulose, a polyethylene oxide and a biologically active ingredient, wherein the amount of ethylcellulose is at least about 15 percent, based on the total weight of the composition.

Another aspect of the present invention is a melt-extruded mono-layered or multi-layered film wherein at least one of the layers is prepared from the above-mentioned biologically active composition.

Yet another aspect of the present invention is an extrudate, prepared from the above-mentioned biologically active composition.

Yet another aspect of the present invention is a process for preparing a melt-extruded mono-layered or multi-layered film which comprises the steps of i) providing the above-mentioned biologically active composition and ii) melt-extruding the composition to a film.

Yet another aspect of the present invention is a process for preparing an extrudate which comprises the steps of i) providing the above-mentioned biologically active composition and ii) melt-extruding the composition.

SHORT DESCRIPTION OF THE DRAWINGS

DETAILED DESCRIPTION OF THE INVENTION

Figure 1:
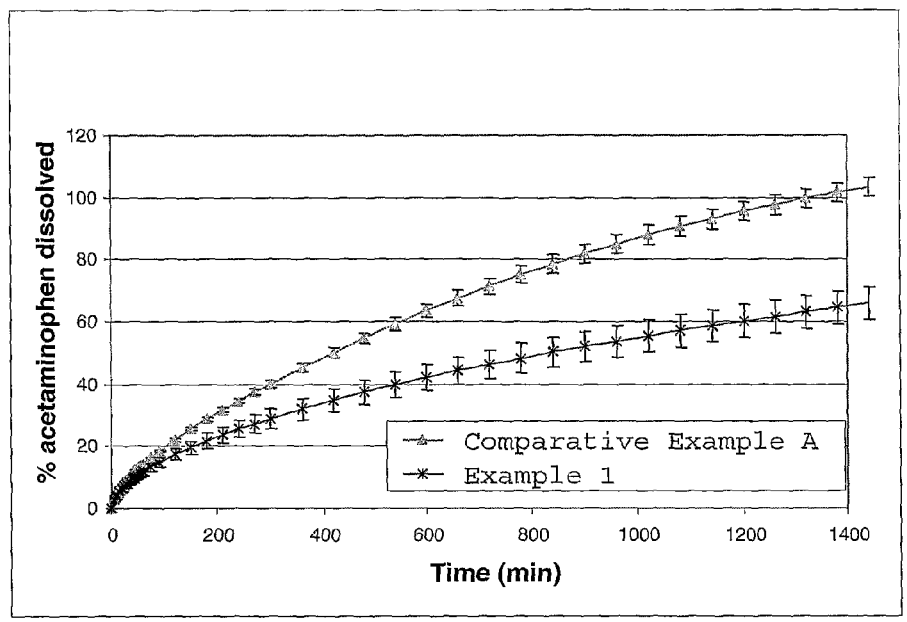
FIG. 1 illustrates the drug release profile of a melt-extruded composition of the present invention and of a comparative composition.

The term "biologically active composition" as used herein encompasses pharmaceutical compositions but also compositions comprising other biologically active ingredients, such as vitamins, herbals and mineral supplements.

It has been found that biologically active compositions which comprise an ethylcellulose, a polyethylene oxide and a biologically active ingredient, wherein the amount of the ethylcellulose is at least about 15 percent, based on the total weight of the composition, can be subjected to melt-extrusion, particularly to hot-melt extrusion. It has also been found that tailor-made release profiles of the biologically active ingredient can be provided. By selecting the amount of ethylcellulose and/or the molecular weight of ethylcellulose, the amount of polyethylene oxide and/or the molecular weight of the polyethylene oxide as taught herein, the release profile of the biologically active ingredient can be controlled and/or adjusted to the specific need. For example, the amount of ethylcellulose and/or the molecular weight of ethylcellulose, the amount of polyethylene oxide and/or the molecular weight of the polyethylene oxide can be adapted to the different amounts and types of the biologically active ingredient and to the different kinds and intervals of administering the biologically active compositions. It has been found that by increasing the percentage of ethylcellulose and/or the molecular weight of the ethylcellulose in the biologically active compositions the release rate of the biologically active ingredient can be decreased and by adjusting the percentage of polyethylene oxide in the composition and the molecular weight of the polyethylene oxide the release rate of the biologically active ingredient can further be adjusted. The present invention allows a wide variety of release profiles without varying the type and amount of biologically active ingredient. It is readily understood by the skilled artisan that providing a wide variety of release profiles is highly desirable. Among others, it allows a controlled adjustment of the release rate of the biologically active ingredient to the specific biologically active ingredient or to the specific need of its administration. Moreover, the inclusion of polyethylene oxide with an average molecular weight at the lower end of the ranges disclosed further below allows for lower processing temperature, extruder torque and pressure during the hot-melt extrusion process. It has also been found that by the present invention the morphology of the biologically active ingredient can generally be influenced. At a high percentage of ethyl cellulose a water soluble biologically active ingredient will generally be in crystalline form in the composition of the present invention, whereas at a high percentage of polyethylene oxide a water soluble biologically active ingredient can be in amorphous form in the composition of the present invention.

The amount of ethylcellulose in the biologically active composition of the present invention is at least about 15 percent, preferably at least about 20 percent, more preferably at least about 25 percent, most preferably at least about 30 percent, based on the total weight of the composition. The amount of ethylcellulose in the biologically active composition of the present invention is generally up to about 95 percent, preferably up to about 85 percent, more preferably up to about 80 percent, most preferably up to about 70 percent, based on the total weight of the composition.

The ethylcellulose preferably has an ethoxyl substitution of from 40 to 55 percent, more preferably from 43 to 53 percent, most preferably from 44 to 51 percent. The percent ethoxyl substitution is based on the weight of the substituted product and determined according to a Zeisel gas chromatographic technique as described in ASTM D4794-94 (2003). The molecular weight of the ethylcellulose is expressed as the viscosity of a 5 weight percent solution of the ethylcellulose measured at 25° C. in a mixture of 80 volume percent toluene and 20 volume percent ethanol. The ethylcellulose concentration is based on the total weight of toluene, ethanol and ethylcellulose. The viscosity is measured using Ubbelohde tubes as outlined in ASTM D914-00 and as further described in ASTM D446-04, which is referenced in ASTM D914-00. The ethylcellulose generally has a viscosity of up to 400 mPa·s, preferably up to 300 mPa·s, more preferably up to 100 mPa·s, measured as a 5 weight percent solution at 25° C. in a mixture of 80 volume percent toluene and 20 volume percent ethanol.

The desirable amount of polyethylene oxide used in the biologically active composition will depend upon a variety of factors, such as its average molecular weight, physical properties, interaction with other components of the composition, ability to solubilize the biologically active ingredient, ease of formulation extrudability, the biological activity of the active ingredient, the indication being treated, the targeted dosing regimen, the projected method of administration, the integrity or stability of the final composition and the desired release profile of the biologically active composition. The amount of the polyethylene oxide in the biologically active composition of the present invention generally is at least about 4.5 percent, preferably at least about 10 percent, more preferably at least about 15 percent, and most preferably at least about 20 percent, based on the total weight of the composition, and generally up to about 84.5 percent, preferably up to about 79 percent, more preferably up to about 70 percent, and most preferably up to about 60 percent, based on the total weight of the composition.

The term "polyethylene oxide" as used herein includes homo- and copolymers of ethylene oxide. The ethylene copolymer may be a random copolymer produced by the polymerization of ethylene oxide mixed with at least one other oxide, such as 1,2-cyclohexene epoxide, 1,2-butene epoxide, allyl glycidyl ether, glycidyl methacrylate, epichlorohydrin, 1,3-butadiene diepoxide, styrene oxide, 4-vinyl-1-cyclohexene 1,2-epoxide, 4-(2-trimethoxysilylethyl)-1,2-epoxycyclohexene and 4-vinyl-1-cyclohexene diepoxide, preferably an alkylene oxide, such as propylene oxide, 1,2-butene epoxide, or isobutylene oxide. Other useful ethylene oxide copolymers are block copolymers produced by the sequential addition of ethylene oxide and at least one other alkylene oxide, in which nearly total consumption of the first monomer takes place prior to the addition of subsequent monomer(s). Alternatively, the ethylene oxide copolymer may comprise in copolymerized form ethylene oxide and another copolymerizable monomer, such as methyl acrylate, ethyl acrylate, a caprolactone, ethylene carbonate, trimethylene carbonate, 1,3-dioxolane, carbon dioxide, carbonyl sulfide, tetrahydrofuran, methyl isocyanate, or methyl isocyanide. Preferred ethylene oxide copolymers are copolymers of ethylene oxide with epichlorohydrin or copolymers of ethylene oxide with cyclohexene oxide. Ethylene oxide copolymers generally comprise at least about 50 mole percent, preferably at least about 70 mole percent, more preferably at least about 85 mole percent ethylene oxide units. The most preferred ethylene oxide polymers are ethylene oxide homopolymers.

The polyethylene oxide preferably has a weight average molecular weight of from about 50,000 to about 10,000,000, more preferably from about 70,000 to about 8,000,000, most preferably from about 90,000 to about 5,000,000. Polyethylene oxides useful in the present composition are commercially available from Union Carbide Corporation, a subsidiary of The Dow Chemical Company. The average molecular weight of the polyethylene oxide employed will generally affect the processing conditions selected. A very high average molecular weight polyethylene oxide, such as greater than about 5,000,000, will generally require higher processing temperature, torque and/or pressure in the extrusion process than a polyethylene oxide having an average molecular weight less than or equal to about 5,000,000.

The weight ratio of the ethylcellulose to the polyethylene oxide is preferably from about 20:1 to about 1:5, more preferably from about 10:1 to about 1:3.

A large variety of biologically active ingredients can be included in the composition of the present invention, such as vitamins, herbals and mineral supplements and drugs. The biologically active ingredient includes hydrophobic, hydrophilic and amphiphilic compounds. It is not necessary for the biologically active ingredient to be soluble in any given component of the composition. The biologically active ingredient may be either dissolved, partially dissolved or suspended in the polymer matrix of the composition. The biologically active ingredient should generally be stable during the melt extrusion process conditions used. By stable, it is meant that a significant portion of the biologically active ingredient will not be significantly degraded or decomposed throughout the melt extrusion process. The biologically active ingredients which may be hot-melt extruded in the compositions of the present invention may be used for treating indications such as, by way of example and without limitation, inflammation, gout, hypercholesterolemia, microbial infection, AIDS, tuberculosis, fungal infection, amoebic infection, parasitic infection, cancer, tumor, organ rejection, diabetes, heart failure, arthritis, asthma, pain, congestion, urinary tract infections, vaginal infection, seizure related disorder, depression, psychosis, convulsion, diabetes, blood coagulation, hypertension and birth control.

Examples of biologically active ingredients that can be administered by the composition of the present invention are, for example, (1) analgesics such as aspirin, ketoprofen, acetaminophen and deflunisal; (2) anesthetics such as lidocaine, procaine, benzocaine and xylocaine; (3) antiarthritics and anti-inflammatory agents such as phenylbutazone, indomethacin, sulindac, dexamethasone, ibuprofen, allopurinol, oxyphenbutazone probenecid, cortisone, hydrocortisone, betamethasone, dexamethasone, fluocortolone, prednisolone, triamncinolone, indomethacin, naproxen and its salts, sulindac and its salts and corresponding sulfide; (4) antiasthma drugs such as theophylline, ephedrine, beclomethasone dipropionate and epinephrine; (5) urinary tract dis-infectives such as sulfarmethoxazole, trimethoprim, nitrofurantoin and norfloxicin; (6) anticoagulants such as heparin, bishydroxy coumarin and warfarin; (7) anticonvulsants such as diphenylhydantoin and diazepam; (8) antidepressants such as amitriptyline, chlordiazepoxide, perphenazine, protriptyline, imipramine and doxepin; (9) agents useful in the treatment of diabetics and regulation of blood sugar, such as insulin, tolbutamide tolazamide, somatotropin, acetohexamide and chlorpropamide; (10) antineoplastics such as adriamycin, fluouracil, methotrexate and asparaginase; (11) antipsychotics such as prochlorperazine, lithium carbonate, lithium citrate, thioridazine, molindone, fluphenazine, trifluoperazine, perphenazine, amitriptyline and triflupromazine; (12) antihypertensives such as spironolactone, methyldopa, hydralazine, clonidine, chlorothiazide, deserpidine, timolol, propranolol, metaprotol, prazosin hydrochloride and reserpine; (13) muscle relaxants such as mephalan, danbrolene, cyclobenzaprine, methocarbamol, diazepam and succinoyl chloride; (14) antiprotozoals such as chloramphenicol, chloroquine and trimethoprim; (15) spermicidals such as nonoxynol; (16) antibacterial substances such as beta-lactam antibiotics, tetracyclines, chloramphenicol, neomycin, cefoxitin, thienamycin, gramicidin, bacitracin, sulfonamides, aminoglycoside antibiotics, tobramycin, nitrofurazone, nalidixic acid and analogs and the antimicrobial combination of flu-dalanine/pentizidone; (17) antihistamines and decongestants such as perilamine, chlorpheniramine, pseudophedrine, phenylephrine, loratidine and tetrahydrozoline; (18) antiparasitic compounds such as ivermectin; and (19) antiviral compounds such as acyclovir and interferon. For treatment of vaginal and urethral conditions requiring antifungal, amoebicidal, trichomonacidal agents or antiprotozoals, the following agents can for example be used polyoxyethylene nonylphenol, alkylaryl sulfonate, oxyquinoline sulfate, miconazole nitrate, sulfanilamide, candicidin, sulfisoxazole, nysatitin, clotrimazole and metronidazole.

The amount of the biologically active ingredient loaded into the composition will vary according to the pharmacological activity of the compound, the indication being treated, the targeted dosing regimen, the projected method of administration, the integrity or stability of the final composition or other such reasons. The amount of the biologically active ingredient generally is at least about 0.5 percent, preferably at least about 1 percent, more preferably at least about 5 percent, most preferably at least about 10 percent, based on the total weight of the composition, and generally up to about 75 percent, preferably up to about 65 percent, more preferably up to about 55 percent, most preferably up to about 45 percent, based on the total weight of the composition. Surprisingly, it has been found that the composition of the present invention in melt-extruded shape can have a high load of the biologically active ingredient, for example 20 percent or more, typically 30 percent or more, in many cases even 45 percent or more, and still release the biologically active ingredient in a controlled or sustained manner from the composition.

The more preferred biologically active compositions of the present invention comprise from about 20 to about 85 percent, most preferably from about 25 to about 80 percent of an ethylcellulose, from about 10 to about 79 percent, most preferably from about 15 to about 70 percent of a polyethylene oxide and from about 1 to about 65 percent, most preferably from about 5 to about 55 percent of a biologically active ingredient, based on the total weight of the ethylcellulose, the polyethylene oxide and the biologically active ingredient, provided that the amount of ethylcellulose is at least about 15 percent, based on the total weight of the composition.

The total weight of the ethylene oxide, polyethylene oxide and biologically active ingredient generally is at least 30, preferably at least 40, more preferably at least 50, and most preferably at least 75 percent of the total weight of the composition.

The biologically active composition may comprise one or more additional components, such as one or more polymers and/or one or more solid or liquid pharmaceutical excipients other than ethylcellulose, polyethylene oxide and a biologically active ingredient, such as one or more fillers, pigments, colorants, flavorants, disintegrating agents, binders, plasticizers, antioxidants and/or lubricants. It is to be understood that some of the useful additional polymers may be known pharmaceutical excipients and that pharmaceutical excipients may be monomeric or polymeric.

Examples of well-known pharmaceutical excipients are acacia, corn starch, guar gum, potato starch, alginic acid, stearic acid, magnesium stearate, lactose, sucrose, dicalcium phosphate, microcrystalline cellulose, sugars, minerals, cellulose powder or cellulose fibers.

Examples of additional polymers are one or more polysaccharides other than ethylcellulose, one or more gelatins, one or more synthetic polymers selected from the group consisting of homo- and copolymers comprising in polymerized form acrylic acid, an acrylic acid salt, acrylamide, vinylalcohol, vinylacetate, vinylpyrrolidone or vinylpyridine, or a combination of one or more polysaccharides, one or more gelatins and/or one or more of said synthetic polymers. Examples of polysaccharides include gum arabic, xanthan gum, gum karaya, gum tragacanth, gum ghatti, carrageenan, dextran, alginates, agar, gellan gum, gallactomannans such as guar gum, pectins, starches, starch derivatives, guar derivatives and xanthan derivatives. Starch derivatives, guar derivatives and xanthan derivatives are described in more detail in European patent EP 0 504 870 B, page 3, lines 25-56 and page 4, lines 1-30. Useful starch derivatives are for example starch ethers, such as hydroxypropyl starch or carboxymethyl starch. Useful guar derivatives are for example carboxymethyl guar, hydroxypropyl guar, carboxymethyl hydroxypropyl guar or cationized guar. Preferred hydroxypropyl guars and the production thereof is described in U.S. Pat. No. 4,645,812, columns 4-6. Preferred polysaccharides are cellulose esters or cellulose ethers other than ethylcellulose. Preferred cellulose ethers are carboxy-$C_1$-$C_3$-alkyl celluloses, such as carboxymethyl celluloses; carboxy-$C_1$-$C_3$-alkyl hydroxy-$C_1$-$C_3$-alkyl celluloses, such as carboxymethyl hydroxyethyl celluloses; $C_1$-$C_3$-alkyl celluloses, such as methylcelluloses; $C_1$-$C_3$-alkyl hydroxy-$C_{1-3}$-alkyl celluloses, such as hydroxyethyl methylcelluloses, hydroxypropyl methylcelluloses or ethyl hydroxyethyl celluloses; hydroxy-$C_{1-3}$-alkyl celluloses, such as hydroxyethyl celluloses or hydroxypropyl celluloses; mixed hydroxy-$C_1$-$C_3$-alkyl celluloses, such as hydroxyethyl hydroxypropyl celluloses, or alkoxy hydroxyethyl hydroxypropyl celluloses, the alkoxy group being straight-chain or branched and containing 2 to 8 carbon atoms. The polysaccharides and the above-mentioned synthetic polymers generally have a weight average molecular weight of at least 10,000, preferably at least 12,000, more preferably at least 15,000. The preferred upper limit for the weight average molecular weight largely depends on the type of polymer. Generally the weight average molecular weight of the additional polymers is up to 1,000,000, preferably up to 500,000, more preferably up to 100,000.

The composition of the present invention is generally melt-extrudable. As used herein, the term "melt-extrudable" refers to a compound or composition that may be melt-extruded, particularly hot-melt extruded. A hot-melt extrudable composition is one that is sufficiently rigid at standard ambient temperature and pressure, when it is not in particulate form such as a powder or granules, but is capable of deformation or forming a semi-liquid state under elevated heat or pressure, that means at a temperature above 25° C. or a pressure above atmospheric pressure. Although the composition of the invention need not contain a plasticizer to render it hot-melt extrudable, plasticizers of the type described herein may be included as one or more additional components. The plasticizer should be able to lower the glass transition temperature or softening point of the biologically active composition in order to allow for lower processing temperature, extruder torque and pressure during the hot-melt extrusion process. Plasticizers also generally reduce the viscosity of a polymer melt thereby allowing for lower processing temperature and extruder torque during hot-melt extrusion. Plasticizers are advantageously included when very high molecular weight polyethylene oxide, such as greater than about 5,000,000, is employed.

The amount of the one or more additional components other than ethylcellulose, polyethylene oxide and a biologically active ingredient, if present in the biologically active composition, is generally not more than 70 percent, preferably not more than 60 percent, more preferably not more than 50 percent, particularly not more than 25 percent, based on the total weight of the composition. The biologically active composition of the present invention is generally melt-extrudable and is preferably used in melt-extruded shape. Preferred melt-extruded shapes are rods, strands, other cross sections, and sheets that can be converted to useful dosage forms via subsequent processing. Preferred shapes are melt-extruded mono-layered or multi-layered films wherein at least one of the layers is prepared from the above-described composition. Other preferred melt-extruded shapes are melt-extruded particles, such as powders, beads, pellets or granules which are prepared from the above-described composition.

The melt-extrusion process, particularly the hot-melt extrusion process for preparing pharmaceutical dosage forms is generally described as follows. A biologically active composition comprising an ethylcellulose, a polyethylene oxide and a biologically active ingredient is provided, wherein the amount of ethylcellulose is at least about 15 percent, based on the total weight of the composition. The composition is provided by mixing the mentioned components, preferably in the form of particles, more preferably in powdered form and optionally admixing one or more of the above-mentioned additional components described above. Preferably additional components are used, if any, that do not hinder the hot-melt extrusion process to a significant extent. Although in some embodiments of the invention the composition to be mixed into the extruder may contain liquid materials, dry feed is advantageously employed in the melt-extrusion process of the present invention. The mixture is fed in an extruder and passed through a heated area of the extruder at a temperature which will melt or soften the composition or at least one or more components thereof to form a matrix throughout which the biologically active ingredient is dispersed. Typical extrusion melt temperatures are from 80 to 210° C., preferably from 90 to 200° C., more preferably from 100 to 190° C. An operating temperature range should be selected that will minimize the degradation or decomposition of the biologically active ingredient and other components of the composition during processing. The extruder used to practice the invention preferably is commercially available model equipped to handle dry feed and having a solid conveying zone, one or multiple heating zones, and an extrusion die. It is particularly advantageous for the extruder to possess multiple separate temperature controllable heating zones. Single or multiple screw extruders, preferably twin screw extruders, can be used in the melt-extrusion process of the present invention.

The molten mixture then exits via a die, or other such element, at which time the mixture (now called the extrudate) begins to harden. The extrudate can exit the die in various shapes, such as a film, sheet, rods, strands or other cross sections. Since the extrudate is still warm or hot upon exiting the die, it may be easily shaped, molded into various shapes, for example into a film, chopped, ground to powders, spheronized into beads or pellets, cut into strands, tableted or otherwise processed to the desired physical form. For example, the extrudate can be processed to various dosage forms by comminuting the extrudate in the shape of a film, sheet or strands into various forms, such as pellets, beads, granules or powders with known means, such as pelletizing, grinding or milling, and converting the particles to a dosage form. If a multilayered film is to be produced, the molded film can be combined with other films layers while it is still warm or hot or after it has been cooled down. Alternately, a multilayered film can be produced via coextrusion, wherein one or more of the layers are produced from the biologically active composition.

Although a melt-extrusion process is preferred, other processes such as injection molding, hot dipping, melt casting, solution casting and compression molding may also be used for producing mono-layered or multilayered films or for producing particles. By using any of these methods, the composition may be shaped as needed according to the desired mode of administration, for example films, such as dermal patches; tablets, pills, lozenges, suppositories, and capsules.

If desired, the melt-extruded composition of the present invention, particularly melt-extruded particles, can be combined with pharmaceutical excipients to produce pharmaceutical dosage forms, such as one or more fillers, pigments, colorants, flavorants, disintegrating agents, binders, plasticizers, antioxidants, lubricants, solid diluents and/or liquid diluents. Examples of useful liquid diluents are oils, water, alcohols, or mixtures thereof, with or without the addition of pharmaceutically suitable surfactants, suspending agents, or emulsifying agents.

The present invention is further illustrated by the following examples which are not to be construed to limit the scope of the invention. Unless otherwise mentioned, all parts and percentages are by weight.

EXAMPLES

The following materials are used for preparing hot melt-extruded compositions:

Ethylcellulose: Ethylcellulose with an ethoxyl content between 48.0 and 49.5 percent. This polymer has a solution viscosity of 9 to 11 cP (mPa·s), measured as a 5 percent solution at 25° C., in an 80/20 mixture of toluene and ethyl alcohol. The ethylcellulose is commercially available under the trademark ETHOCEL™ Standard 10 Premium from The Dow Chemical Company.

POLYOX™ 301 WSR: A polyethylene oxide having a weight average molecular weight of about 4,000,000 which is commercially available under the trademark POLYOX™ 301 WSR from Union Carbide Company, a subsidiary of The Dow Chemical Company.

POLYOX™ N-10 WSR: A polyethylene oxide having a weight average molecular weight of about 100,000 which is commercially available under the trademark POLYOX™ N-10 WSR from Union Carbide Company, a subsidiary of The Dow Chemical Company.

HPMC E5: A hydroxypropyl methyl cellulose having a methoxyl content of 28-30 percent, a hydroxypropoxyl content of about 8 percent and a viscosity of 4-6 mPa·s, measured as a 2 weight percent aqueous solution using a Brookfield viscosimeter at 20° C. It is commercially available from The Dow Chemical Company under the Trademark METHOCEL E5 Premium LV.

Acetaminophen: A drug that is generally used to relieve mild to moderate pain and to reduce fever. Acetaminophen has an aqueous solubility of 14 mg/ml and is USP classified as sparingly soluble.

Ketoprofen: A drug that is generally used to relieve mild to moderate pain, to reduce inflammation and to reduce fever. Ketoprofen has an aqueous solubility of 0.294 mg/ml and is USP classified as very slightly soluble.

Nifedipine: A drug that is generally used in the treatment of angina pectoris and hypertension. Nifedipine has an aqueous solubility of <0.1 mg/ml at 20° C.

All drugs are commercially available from Spectrum Chemical & Laboratory Products Inc., California, USA.

The comparative Examples below are not within the scope of the present invention but do not necessarily present prior art.

Example 1

37.5 weight parts of ethylcellulose, 12.5 weight parts of POLYOX™ 301 WSR and 50 weight parts of acetaminophen are blended for 10 minutes using a V-blender. This blend is then extruded via a ¾ inch (1.9 cm) single screw extruder of a length/diameter ratio of 28:1 equipped with a rod die of a diameter of 0.325 inch (0.8 cm). The processing conditions in the extruder are: 110° C. in zone 1, 150° C. in zone 2, 150° C. in zone 3, the die temperature is 150° C. and the speed of the extruder screw is 100 rpm. The extruded rod is opaque and light tan in color. Tablets of 300 to 500 mg are cut from the rod immediately after processing.

Comparative Example A

Example 1 is repeated, except that 50 weight parts of POLYOX™ 301 WSR and 50 weight parts of acetaminophen are blended and extruded. The extrudate is clear with some small opaque areas.

Comparative Example B1

Example 1 is repeated, except that 50 weight parts of ethylcellulose and 50 weight parts of acetaminophen are blended. The blend is extruded in the same extruder as in Example 1, but with the following temperature conditions: 120° C. in zone 1, 170° C. in zone 2, 170° C. in zone 3, and die temperature of 170° C. No extrudate is recovered, as the mixture does not convey through the extruder.

Comparative Example B2

The extrusion is also tried with the following temperature conditions: 90° C. in zone 1, 160° C. in zone 2, 190° C. in zone 3, and die temperature of 190° C. Again, no extrudate is recovered due to poor processing.

Comparative Examples C1 and C2

25 weight parts of ethylcellulose and 75 weight parts of acetaminophen are blended. In two extrusion trials the processing conditions of Comparative Examples B1 and B2 are used. Both extrusion trials fail.

The results of Comparative Examples B1, B2, C1 and C2 illustrate that blends of ethylcellulose and the well-known drug acetaminophen are very difficult to extrude, presumably due to incompatibility between the polymer and drug.

Drug Release Testing of Example 1 and Comparative Example A

Dissolution testing is performed with a Distek TCS0200B dissolution system equipped with a Hewlett-Packard 8452A Diode Array Spectrophotometer. The wavelength used for acetaminophen is 242 to 244 nm. All dissolution tests are done in 900 mL deaerated (Distek MD-1 De-Gasser) phosphate buffer (pH 5.8). The dissolution media temperature is 37±0.5° C. USP Apparatus II is used (paddles) with a rotation speed of 50 rpm. Six replicate samples are run for each dissolution test.

The dissolution results are illustrated in FIG. 1. Total acetaminophen release occurs at about 1400 minutes for the 50/50 POLYOX™ WSR 301/acetaminophen sample. A significant difference is observed when ethylcellulose is added to the composition. At 1400 minutes, only about 65 percent of the acetaminophen has been released.

Example 2

60 weight parts of ethylcellulose, 20 weight parts of POLYOX™ 301 WSR and 20 weight parts of ketoprofen are blended for 10 minutes using a V-blender. This blend is then extruded in the same extruder as in Example 1. The processing temperatures are: 60° C. in zone 1, 90° C. in zone 2, 150° C. in zone 3, and the die temperature is 150° C. The extruded rod is opaque and off white in color. Tablets of 300 to 500 mg are cut from the rod immediately after processing.

Comparative Example D

Example 2 is repeated, except that 95 weight parts of POLYOX™ 301 WSR and 5 weight parts of ketoprofen are blended and extruded. The processing temperatures are: 100° C. in zone 1, 140° C. in zone 2, 150° C. in zone 3, and the die temperature is 150° C. The extruded rod is transparent when exiting the die but turns opaque, white shortly thereafter.

Comparative Example E

Example 2 is repeated, except that 80 weight parts of POLYOX™ 301 WSR and 20 weight parts of ketoprofen are blended and extruded. The processing temperatures are: 120° C. in zone 1, 150° C. in zone 2, 150° C. in zone 3, and the die temperature is 150° C. The extruded rod is transparent and amber in color.

Figure 2:
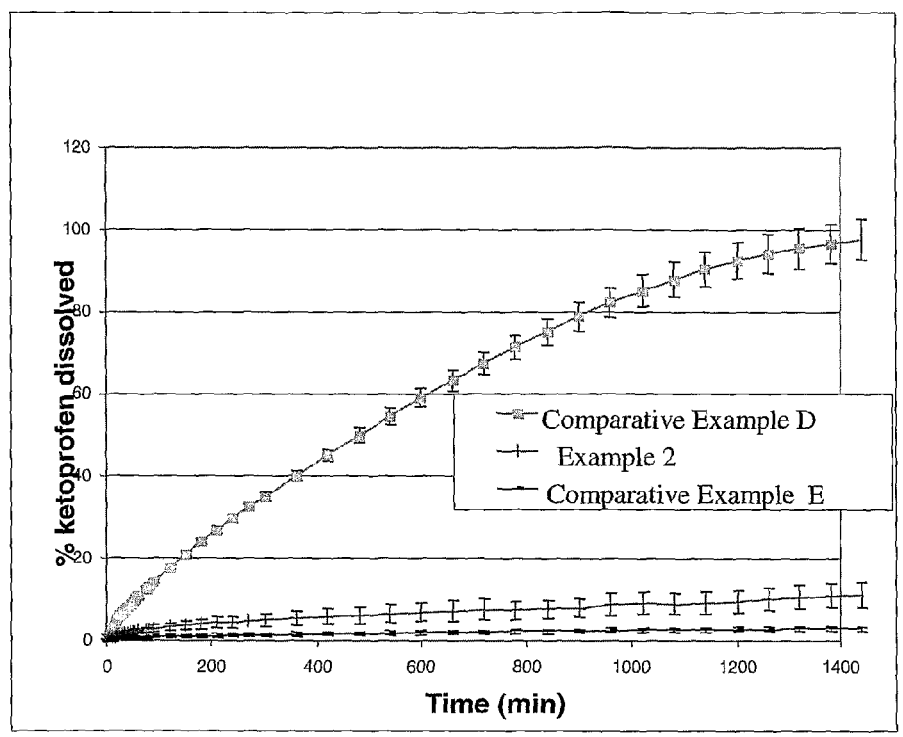
FIG. 2 illustrates the drug release profile of another melt-extruded composition of the present invention and of two other comparative compositions.

The drug release testing of Example 2 and Comparative Examples D and E is done as in Example 1 except that the wavelength used for ketoprofen is 258 to 262 nm and the dissolution media is simulated intestinal fluid (pH 7.4). The ketoprofen dissolution data are shown in FIG. 2. The results illustrate that tailored drug release profiles can be obtained by combining a polyethylene oxide with ethylcellulose.

Example 3

40 weight parts of ethylcellulose, 10 weight parts of POLYOX™ N-11 WSR and 50 weight parts of ketoprofen are blended for 10 minutes using a V-blender. The blend is fed via a K-tron volumetric feeder at a rate of 19.23 g/min into a C. W. Brabender Conical Twin Screw Extruder model PL2000 equipped with a 5 mm diameter rod die. The processing conditions are: 60° C. in zone 1, 90° C. in zone 2, 150° C. in zone 3, the die temperature is 150° C. and the speed of the extruder screw is 30 rpm. The extruded rod is opaque and cream orange in color. Tablets of 300 to 500 mg are cut from the rod immediately after processing.

Example 4

Example 3 is repeated, except that 37.5 weight parts of ethylcellulose, 12.5 weight parts of POLYOX™ 301 WSR and 50 weight parts of ketoprofen are blended and fed into the Twin Screw Extruder at a rate of 12.21 g/min. The processing temperatures are: 80° C. in zone 1, 150° C. in zone 2, 150° C. in zone 3, and the die temperature is 150° C. The extruded rod is clear amber in color.

Comparative Example F

Example 3 is repeated, except that 80 weight parts of POLYOX™ N-10 WSR and 20 weight parts of ketoprofen are blended and fed into the Twin Screw Extruder at a rate of 20.04 g/min. The processing temperatures are: 80° C. in zone 1, 120° C. in zone 2, 120° C. in zone 3, and the die temperature is 120° C. The extruded rod is cream yellow in color.

Comparative Example G

Example 3 is repeated, except that 80 weight parts of ethylcellulose and 20 weight parts of ketoprofen are blended and fed into the Twin Screw Extruder at a rate of 23.71 g/min. The processing temperatures are: 80° C. in zone 1, 100° C. in zone 2, 100° C. in zone 3, and the die temperature is 100° C. The extruded rod is cream yellow in color.

Comparative Example H

Example 3 is repeated, except that 50 weight parts of POLYOX™ 301 WSR and 50 weight parts of ketoprofen are blended and fed into the Twin Screw Extruder at a rate of 19.95 g/min. The processing temperatures are: 80° C. in zone 1, 150° C. in zone 2, 150° C. in zone 3, and the die temperature is 150° C. The extruded rod is grayish white in color.

Figure 3:
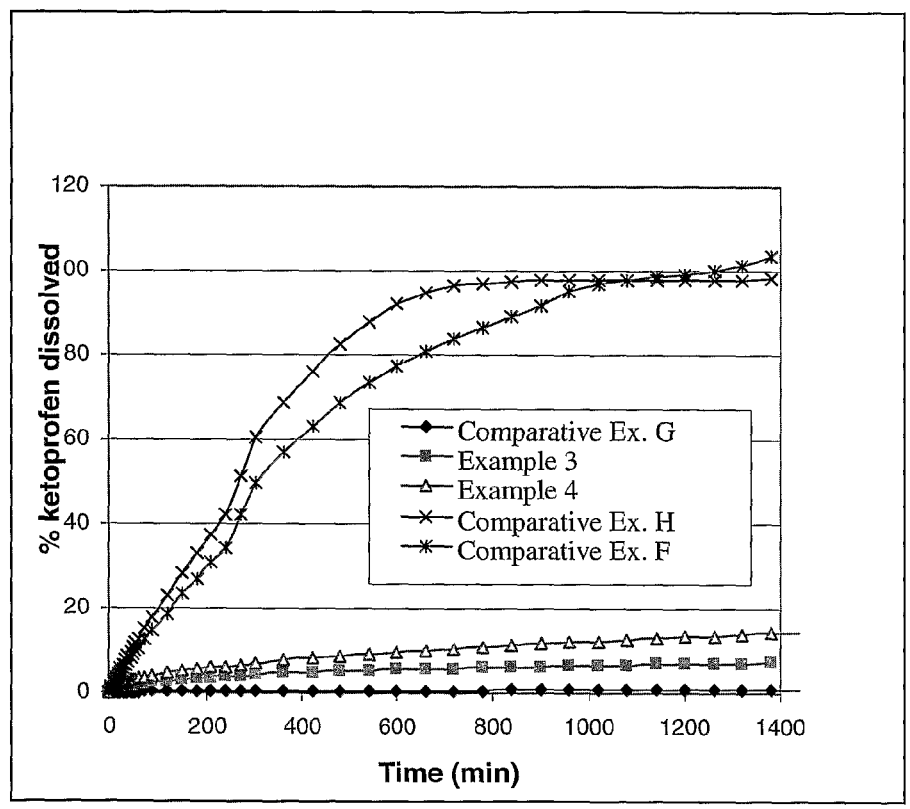
FIG. 3 illustrates the drug release profile of two other melt-extruded compositions of the present invention and of three other comparative compositions.
Figure 4:
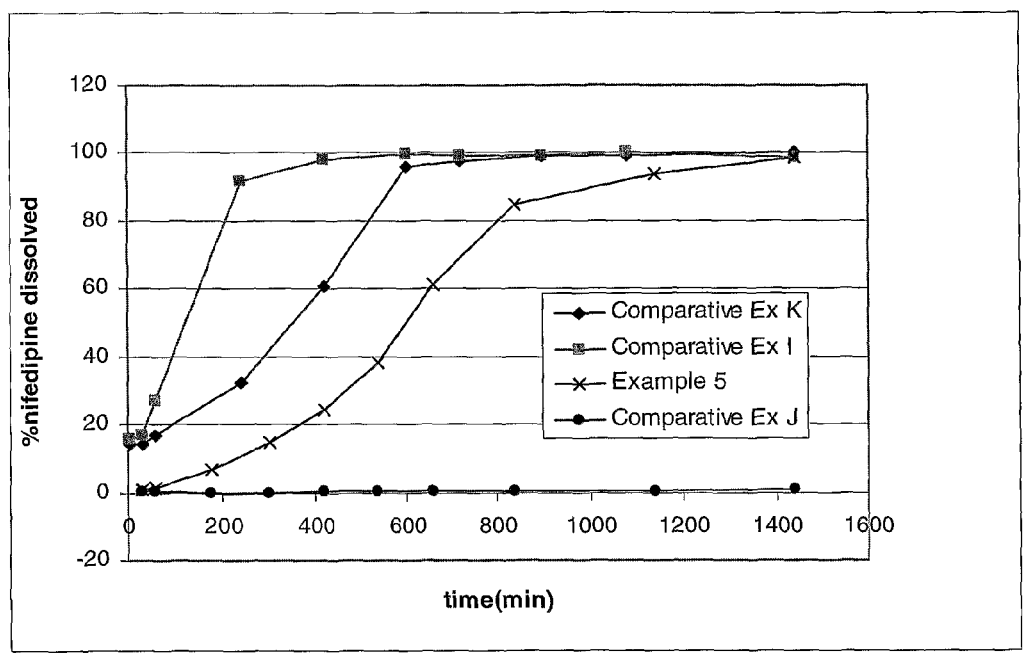
FIG. 4 illustrates the dissolution results and that tailored drug release profiles can be obtained by combining a polyethylene oxide with ethylcellulose in the presence of a third polymer, such as a cellulose ether other than ethylcellulose.

The drug release testing of Examples 3 and 4 and of Comparative Examples F to H is done as in Example 2. The ketoprofen dissolution data are shown in FIG. 3. The results illustrate that tailored drug release profiles can be obtained by combining a polyethylene oxide with ethylcellulose.

Example 5

36 weight parts of POLYOX™ N-10 WSR, 28 weight parts of HPMC E5, 16 weight parts of ethylcellulose, and 20 weight parts of nifedipine are blended for 10 minutes using a V-blender. The blend is dried in a vacuum oven at 50° C. for 16 hours prior to extrusion. This blend is then extruded via a ¾ inch (1.9 cm) single screw extruder of a length/diameter ratio of 28:1 equipped with a rod die of a diameter of 0.325 inch (0.8 cm). The processing conditions in the extruder are: 130° C. in zone 1, 175° C. in zone 2, 175° C. in zone 3, the die temperature is 175° C. and the speed of the extruder screw is 100 rpm. The extrudate is opaque and yellow in color. Tablets of 300 to 500 mg are cut from the rod immediately after processing.

Comparative Example I

Example 5 is repeated, except that 80 weight parts of POLYOX™ N-10 WSR and 20 weight parts of nifedipine are blended and extruded. The extrusion conditions are 80° C. in zone 1, 170° C. in zone 2, 205° C. in zone 3, the die temperature is 205° C. and the speed of the extruder is 100 rpm. The extrudate is opaque and yellow in color. Tablets of 300 to 500 mg are cut from the rod immediately after processing.

Comparative Example J

Example 5 is repeated, except that 80 weight parts of ethylcellulose and 20 weight parts of nifedipine are blended and extruded. The extrusion conditions are 130° C. in zone 1, 175° C. in zone 2, 175° C. in zone 3, the die temperature is 175° C. and the speed of the extruder is 100 rpm. The extrudate is yellow in color, with some small opaque areas. Tablets of 300 to 500 mg are cut from the rod immediately after processing.

Comparative Example K

Example 5 is repeated, except that 40 weight parts of HPMC E5, 40 weight parts of POLYOX™ N-10 WSR and 20 weight parts of nifedipine are blended and extruded. The blend is dried in a vacuum oven at 50° C. for 16 hours prior to extrusion. The extrusion conditions are 80° C. in zone 1, 170° C. in zone 2, 205° C. in zone 3, the die temperature is 205° C. and the speed of the extruder is 100 rpm. The extrudate is opaque and yellow in color. Tablets of 300 to 500 mg are cut from the rod immediately after processing.

Drug Release Testing of Example 5 and Comparative Examples I, J, and K

Dissolution testing is performed with a Distek D12604095 dissolution system equipped with an Autosampler venkel, serial #17-695-0298. All dissolution tests are done in 900 mL 1% sodium lauryl sulfate buffer. The dissolution media temperature is 37±0.5° C. USP Apparatus II is used (paddles) with a rotation speed of 50 rpm. Samples are collected at 30, 60, 180, 300, 420, 540, 660, 840, 1140, and 1440 minutes of the dissolution experiment for HPLC analysis. Six replicate samples are run for each dissolution test.

The samples from the dissolutions are filtered through 0.45 micron nylon filters. Filtered samples are analyzed using an Agilent 1100 series HPLC. The mobile phase is a 50:50 blend of acetonitrile and microfiltrated water. An injection volume of 25 microliters is used. The HPLC pump has a flow rate of 1 mL/min and the analysis lasts three minutes. The wavelength used to evaluate nifedipine is 236 nm. No column is used for the analysis. The oven temperature is 30° C. Hewlett Packard Chemstation software was used to collect the data.

The invention claimed is:
1. A melt-extruded mono-layered or multi-layered film wherein at least one of the layers is prepared from a biologically active composition comprising a mixture of an ethylcellulose, an ethylene oxide homo- or copolymer having a weight average molecular weight of from about 50,000 to about 10,000,000 and a biologically active ingredient, wherein in said at least one layer the amount of ethylcellulose is at least 25 percent and the amount of the ethylene oxide homo- or copolymer is at least 10 percent, based on the total weight of the composition, and the total weight of ethylcellulose, ethylene oxide homo- or copolymer and biologically active ingredient is at least 50 percent, based on the total weight of the composition, with the proviso that the composition does not contain hydroxypropyl cellulose.

2. The melt-extruded mono-layered or multi-layered film of claim 1 wherein the amount of ethylcellulose in said at least one layer is at least 30 percent, based on the total weight of the composition.

3. The melt-extruded mono-layered or multi-layered film of claim 1 wherein the weight ratio of the ethylcellulose to the ethylene oxide homo- or copolymer in said at least one layer is from about 10:1 to about 1:3.

4. A biologically active composition in a melt-extruded shape comprising a mixture of an ethylcellulose, an ethylene oxide homo- or copolymer having a weight average molecular weight of from about 50,000 to about 10,000,000 and a biologically active ingredient, wherein the amount of ethylcellulose is at least 25 percent and the amount of the ethylene oxide homo- or copolymer is at least 10 percent, based on the total weight of the composition and the total weight of ethylcellulose, ethylene oxide homo- or copolymer and biologically active ingredient is at least 50 percent, based on the total weight of the composition, with the proviso that the composition does not contain hydroxypropyl cellulose, said melt-extruded shape being in the shape of melt-extruded rods, strands, or particles.

5. The composition of claim 4 wherein the weight ratio of the ethylcellulose to the ethylene oxide homo- or copolymer is from about 10:1 to about 1:3.

6. The composition of claim 4 wherein the amount of ethylcellulose is at least 30 percent, based on the total weight of the composition.

7. The melt-extruded film of claim 1 being a mono-layered film.

* * * * *